United States Patent
Oleksy et al.

(12) 
(10) Patent No.: US 7,642,390 B2
(45) Date of Patent: Jan. 5, 2010

(54) EB/SM SPLITTER HEAT RECOVERY

(75) Inventors: Slawomir A. Oleksy, Billerica, MA (US); Vincent A. Welch, Medway, MA (US); Leslie F. Whittle, Windham, NH (US)

(73) Assignee: Stone & Webster, Inc., Houston, TX (US)

( * ) Notice: Subject to any disclaimer, the term of this patent is extended or adjusted under 35 U.S.C. 154(b) by 930 days.

(21) Appl. No.: 10/517,734

(22) PCT Filed: Jun. 5, 2003

(86) PCT No.: PCT/US03/17944

§ 371 (c)(1),
(2), (4) Date: Dec. 8, 2004

(87) PCT Pub. No.: WO03/106389

PCT Pub. Date: Dec. 24, 2003

(65) Prior Publication Data

US 2005/0245779 A1    Nov. 3, 2005

(51) Int. Cl.
*C07C 5/02*    (2006.01)
(52) U.S. Cl. .................. 585/441; 585/440; 585/442; 585/443
(58) Field of Classification Search .............. 585/441, 585/440, 442, 443
See application file for complete search history.

(56) References Cited

U.S. PATENT DOCUMENTS

| | | | |
|---|---|---|---|
| 3,256,355 A * | 6/1966 | Gilman et al. | ............... 585/441 |
| 4,628,136 A | 12/1986 | Sardina | |
| 4,695,664 A | 9/1987 | Whittle | |
| 5,255,742 A | 10/1993 | Mikus | |
| 5,386,075 A | 1/1995 | Keil et al. | |
| 5,404,952 A | 4/1995 | Vinegar et al. | |
| 5,659,095 A | 8/1997 | Friedman et al. | |
| 6,171,449 B1 * | 1/2001 | Welch | ........... 202/154 |
| 6,222,080 B1 | 4/2001 | Friedman et al. | |
| 6,287,483 B1 | 9/2001 | DeMassa et al. | |
| 6,300,533 B1 | 10/2001 | Benage et al. | |
| 6,388,155 B1 * | 5/2002 | Sy et al. | ............. 585/441 |

FOREIGN PATENT DOCUMENTS

EP    0 747 335 A1    12/1996

* cited by examiner

*Primary Examiner*—Tam M Nguyen
(74) *Attorney, Agent, or Firm*—Alan B. Clement; Peter J. Fallon; Locke Lord Bissell & Liddell LLP

(57) ABSTRACT

Improved methods and related apparatus are disclosed for efficiently recovering the heat of condensation from overhead vapor produced during separation of various components of dehydrogenation reaction effluent, particularly in ethylbenzene-to-styrene operations, by the use of at least a compressor to facilitate azeotropic vaporization of an ethylbenzene and water mixture within a preferred range of pressure/temperature conditions so as to minimize undesired polymerization reactions.

14 Claims, 4 Drawing Sheets

Process Flow Diagram for Scheme 1

Legend
101 Steam Superheater
102 Dehydrogenation Reactor System
103 Feed/Effluent Heat Exchange
104 Effluent Heat Recovery
105 Effluent Condenser
106 Phase Separator
107 Fractionator
108 Azeotropic Mixture Vaporizer
109 Azeotropic Mixture Compressor Figure 1. Process Flow Diagram for Scheme 1

Legend
101 Steam Superheater
102 Dehydrogenation Reactor System
103 Feed/Effluent Heat Exchange
104 Effluent Heat Recovery
105 Effluent Condenser
106 Phase Separator
107 Fractionator
108 Azeotropic Mixture Vaporizer
109 Azeotropic Mixture Compressor Figure 2. Process Flow Diagram for Scheme 2

Legend
101 Steam Superheater
102 Dehydrogenation Reactor System
103 Feed/Effluent Heat Exchange
104 Effluent Heat Recovery
105 Effluent Condenser
106 Phase Separator
107 Fractionator
108 Azeotropic Mixture Vaporizer
109 Fractionator Overhead Compressor Figure 3. Process Flow Diagram for Scheme 3

Legend
101 Steam Superheater
102 Dehydrogenation Reactor System
103 Feed/Effluent Heat Exchange
104 Effluent Heat Recovery
105 Effluent Condenser
106 Phase Separator
107 Fractionator
108 Azeotropic Mixture Vaporizer
109 Azeotropic Mixture Compressor
110 Fractionator Overhead Compressor

EB/SM SPLITTER HEAT RECOVERY

FIELD OF THE INVENTION

The present invention relates to a low temperature heat recovery technique in the process of making styrene through dehydrogenation of ethylbenzene at elevated temperatures in the presence of steam. Specifically, this invention teaches methods of recovering the heat of condensation from the overhead vapor leaving the distillation column which is used for separation of unreacted ethylbenzene from the styrene product (hereinafter referred to as the EB/SM splitter) together with related apparatus. Typically, this heat is rejected to atmosphere through the use of cooling water or air fins and is therefore wasted. The EB/SM splitter typically has a heat removal requirement of between 400 and 700 kcal/kg of styrene product, which represents a significant portion of the overall cost of styrene production. Recovery of a substantial portion of this thermal energy dramatically improves operating economics and process efficiencies.

BACKGROUND OF THE INVENTION

U.S. Pat. No. 6,171,449 teaches methods of recovering at least a portion of the heat contained in an EB/SM splitter overhead stream via use of a cascade reboiler scheme in which the separation of ethylbenzene and styrene is carried out in two parallel distillation columns operating at different pressures, with the overhead of the high pressure column providing the heat required to reboil the low pressure column.

In contrast, U.S. Pat. No. 4,628,136 teaches a method of recovering the heat contained in the overhead of the EB/SM splitter by using this stream to boil an azeotropic mixture of ethylbenzene and water, which, once vaporized, is subsequently transferred to the reaction system where dehydrogenation of ethylbenzene to styrene takes place. The method described in the U.S. Pat. No. 4,628,136 patent, however, requires that the EB/SM splitter operate at a pressure that is sufficiently high as to enable the transfer of the azeotropic mixture of ethylbenzene and water vapor into the reactor system without the use of a compressor. This patent also specifies that the temperature difference between the condensing EB/SM splitter overhead and the boiling azeotropic mixture of ethylbenzene and water should be in the range of between and 2 and 10° C. Given this temperature constraint, one can derive a relationship between the pressure at which the azeotropic vaporization is taking place and the required overhead pressure of the EB/SM splitter. This relationship is presented graphically in FIG. 4.

As can be seen in the graph presented in FIG. 4, the method taught by U.S. Pat. No. 4,628,136 requires that the EB/SM splitter operate at an overhead pressure of at least 200 mmHg in order for the azeotropic mixture to be transferred into the reactor system without the use of the compressor. This is because the practical lower limit for the pressure at the inlet of the reactor system is of the order of 400 mmHg, and may range up to about 1100 mmHg, which must be increased by another 100 to 200 mmHg in order to pass the azeotropic mixture of ethylbenzene and water vapor through the heat exchange system (e.g., reactor feed-effluent exchanger or a fired heater) which is needed to bring it to the required reaction temperature and to pass this stream into and through the reactor system. As a consequence of this limitation, the method taught by U.S. Pat. No. 4,628,136 results in required operating temperatures for the EB/SM splitter which are significantly higher than in a conventional process where no effort is made to recover heat from the overhead. Operation at such higher temperature and pressure, however, is more costly both in operational and capital costs.

The necessary increase in operating temperature and pressure which is required to practice the method of the U.S. Pat. No. 4,628,136 patent also leads to an increase in the rate of styrene polymerization which is a direct yield loss. For uninhibited styrene monomer, the polymerization rates approximately double for every 7 to 8° C. increase in temperature. In commercial practice, the method taught by U.S. Pat. No. 4,628,136 results in operating the EB/SM splitter at temperatures on the order of 20° C. to 30° C. higher than conventional technology. The net result is either the need for increased dosage rates of costly polymerization inhibitors or accepting an increased formation of undesired styrene polymer (yield loss), or both, resulting in a substantial negative impact on the overall process economics. Furthermore, the close-coupling of the EB/SM splitter and the dehydrogenation reactor system operations required to practice the method of the U.S. Pat. No. 4,628,136 patent means that an increase in pressure drop anywhere in the reaction system (as for example that which may be caused by fouling of heat exchange surfaces or by catalyst attrition leading to higher pressure drop in the catalyst beds) will require that the EB/SM splitter be operated under even higher pressure and temperature conditions than usual, resulting in still further increases in polymerization inhibitor consumption, styrene polymer byproduct, or both.

These and other deficiencies in or limitations of the prior art are overcome in whole or in part by the improved method and related apparatus of the present invention.

SUMMARY OF THE INVENTION

In a principal embodiment of the new invention described herein, it has been found that the aforementioned limitations of the method taught by U.S. Pat. No. 4,628,136 can be overcome by use of a compressor. Using a compressor at one or more selected locations in the process flow scheme realizes a number of important and unexpected benefits over the prior art including: a) it allows the EB/SM splitter to operate at a substantially lower pressure and temperature; b) it compensates for any reasonable pressure drop increases in the reaction section; c) it allows the EB/SM splitter operating conditions to be set independently from the reaction section of the overall process; d) it allows higher differential temperatures between the condensing overhead and the vaporizing azeotrope, resulting in smaller heat transfer area requirements; and e) it allows recovery of substantially all of the usable heat contained in the overhead stream.

The general concept of using of a compressor for transferring an azeotropic mixture of ethylbenzene and water vapor into the dehydrogenation reactor system was taught earlier by U.S. Pat. No. 4,695,664. However, in the method taught in the U.S. Pat. No. 4,695,664 patent, the azeotropic mixture of ethylbenzene and water is boiled by heat exchange with the reactor effluent rather than using the EB/SM splitter overhead, as taught by this invention, to provide the necessary heat. As a consequence of this difference, in the practice of the U.S. Pat. No. 4,695,664 patent the pressure of the azeotropic mixture should be maintained at about 200 mmHg. Pressures higher than this are undesirable because of the need to operate the dehydrogenation reactors at a higher pressure (requiring more catalyst and more steam to maintain catalyst stability), while operating the system at pressures lower than 200 mmHg makes compression costs prohibitively expensive. In contrast, the method of the present invention can be practiced at a higher azeotropic mixture pressure, in the range of about 150 to 600 mmHg, preferably about 250 to 390 mmHg, limited only by the polymerization considerations in the EB/SM splitter.

Thus, the unique features of the methods and apparatus of the present invention allow the azeotropic vaporization of the EB/water mixture to take place in the pressure range of about 150 to 600 mmHg, preferably a range of about 250 to 390 mmHg, which largely falls outside the acceptable pressure ranges taught by prior art methods. In addition, other unexpected efficiencies and economies are realized with the methods and apparatus of this invention as described hereinafter.

DESCRIPTION OF THE PREFERRED EMBODIMENTS

The methods and apparatus of this invention pertain to catalyzed hydrocarbon dehydrogenation processes, for example the process of manufacturing styrene via dehydrogenation of ethylbenzene in the presence of steam at elevated temperatures in a reactor system typically containing an iron oxide based dehydrogenation catalyst.

Figure 1:
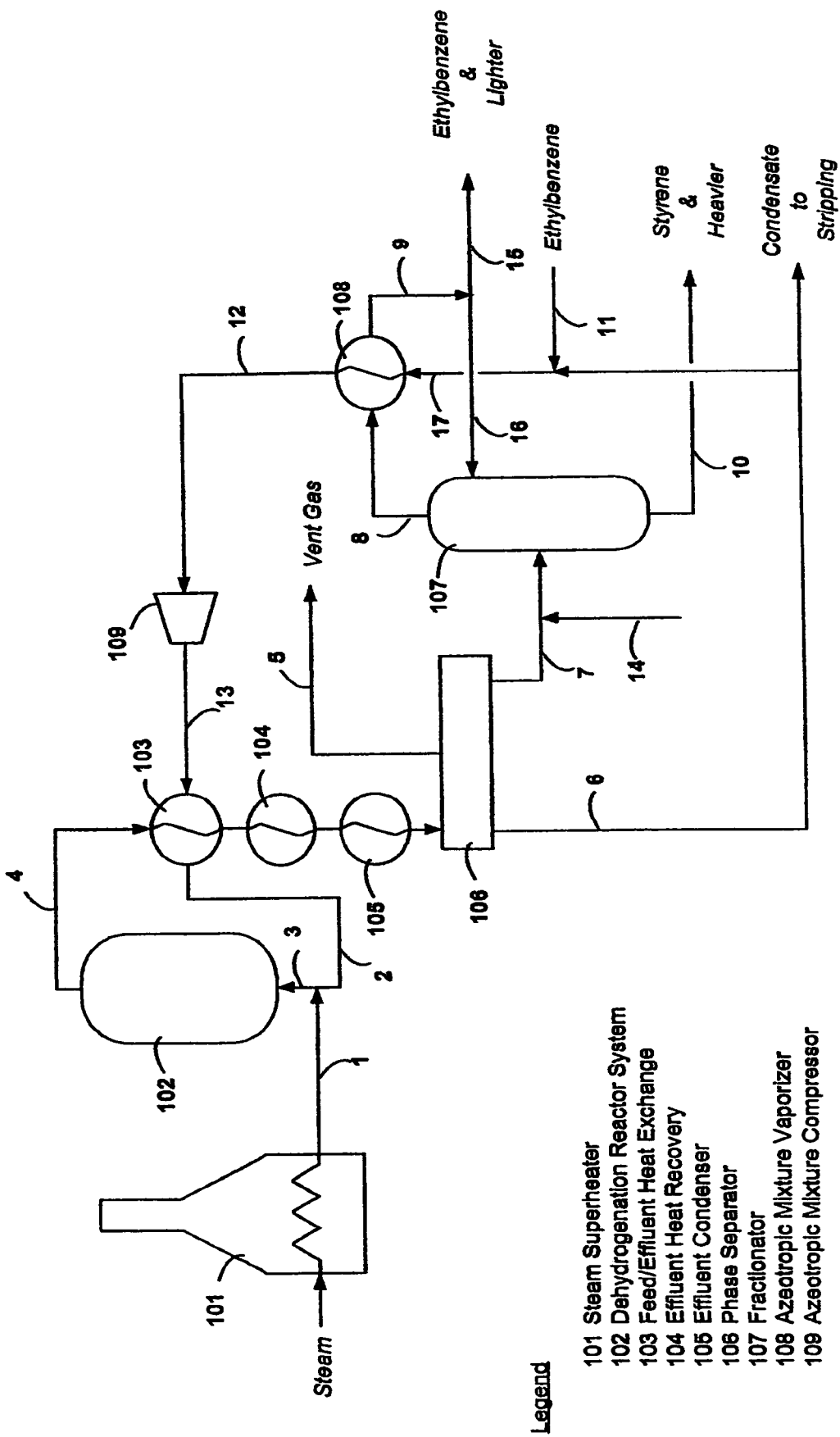
FIG. 1 is a process flow diagram of a first embodiment of the present invention wherein a compressor unit is located in-line between the condenser downstream of the fractionator and the dehydrogenation reactor.

A first embodiment of this invention, as applied to the manufacture of styrene by the above process, is illustrated in FIG. 1. In this embodiment, a gaseous mixture 2 of ethylbenzene and steam is mixed with additional steam 1 which has been preheated to a temperature of typically between about 700 and 900° C. in a fired steam superheater 101. The resulting mixture 3 is passed through a dehydrogenation system 102 comprising one or more dehydrogenation reactors together with a means of supplying heat to compensate for heat lost due to the endothermic nature of the dehydrogenation reaction. The reactors can be either isothermal or adiabatic, and the heat can be added either directly (e.g., by passing the reaction mixture through a fired heater or through flameless distributed combustion tubes, as described for example in U.S. Pat. Nos. 5,255,742 and 5,404,952, which patents are incorporated herein by reference), or indirectly, by contacting the reaction mixture with a heat carrying medium such as steam, molten salt or flue gas in a shell and tube heat exchanger. The dehydrogenation reaction is carried out at a temperature of between about 500 and 700° C., preferably between about 550 and 650° C., and at a pressure of between about 0.3 and 2 atmospheres, preferably between about 0.3 and 0.8 atmospheres, and preferably in the presence of a iron oxide based dehydrogenation catalyst, examples of which include catalysts commonly referred to by their trade names of Styromax 3, Hypercat, and D-0239E, as is well-known in this art. The overall molar ratio of steam to ethylbenzene in the reactor feed 3 is typically between about 5 and 15. Lower ratios are preferred because of reduced steam cost, reduced effluent condensation cost, and investment savings resulting from smaller equipment. The minimum steam to ethylbenzene ratio at which the process can be carried out depends on a variety of factors, including catalyst stability and on metal structural temperature limits in the steam superheater 101 and the dehydrogenation system 102.

The reactor effluent 4 is cooled in a feed/effluent heat exchanger 103 where it exchanges heat with the relatively cold reactor feed 13. It is then cooled further in a steam generator 104 and at least partially condensed in a condenser 105 using either air or cooling water as a cooling medium (not shown). The partially condensed effluent flows into a phase separator 106 where the dehydrogenation vent gas 5 is separated from the liquids. The liquids coming from separator 106 are then decanted into a hydrocarbon stream 7 and an aqueous condensate stream 6. The hydrocarbon stream 7, often referred to as a crude styrene stream, contains a mixture of styrene, unreacted ethylbenzene, and water/steam, as well as reaction byproducts such as benzene, toluene and various high boiling compounds which may include alpha-methylstyrene, divinylbenzene, and dicyclics (e.g., stilbene).

The crude styrene stream 7 is then typically processed in a series of distillation columns for separating out various light and heavy fractions. The first step in this process typically involves removing benzene and toluene from the balance of the mixture, followed by a second step in which unreacted ethylbenzene is recovered. Alternatively, ethylbenzene may be removed together with benzene and toluene in the first step, and then be separated from these lighter components in the second step. In either scheme, the last distillation step involves separation of styrene from the heavier components.

Figure 2:
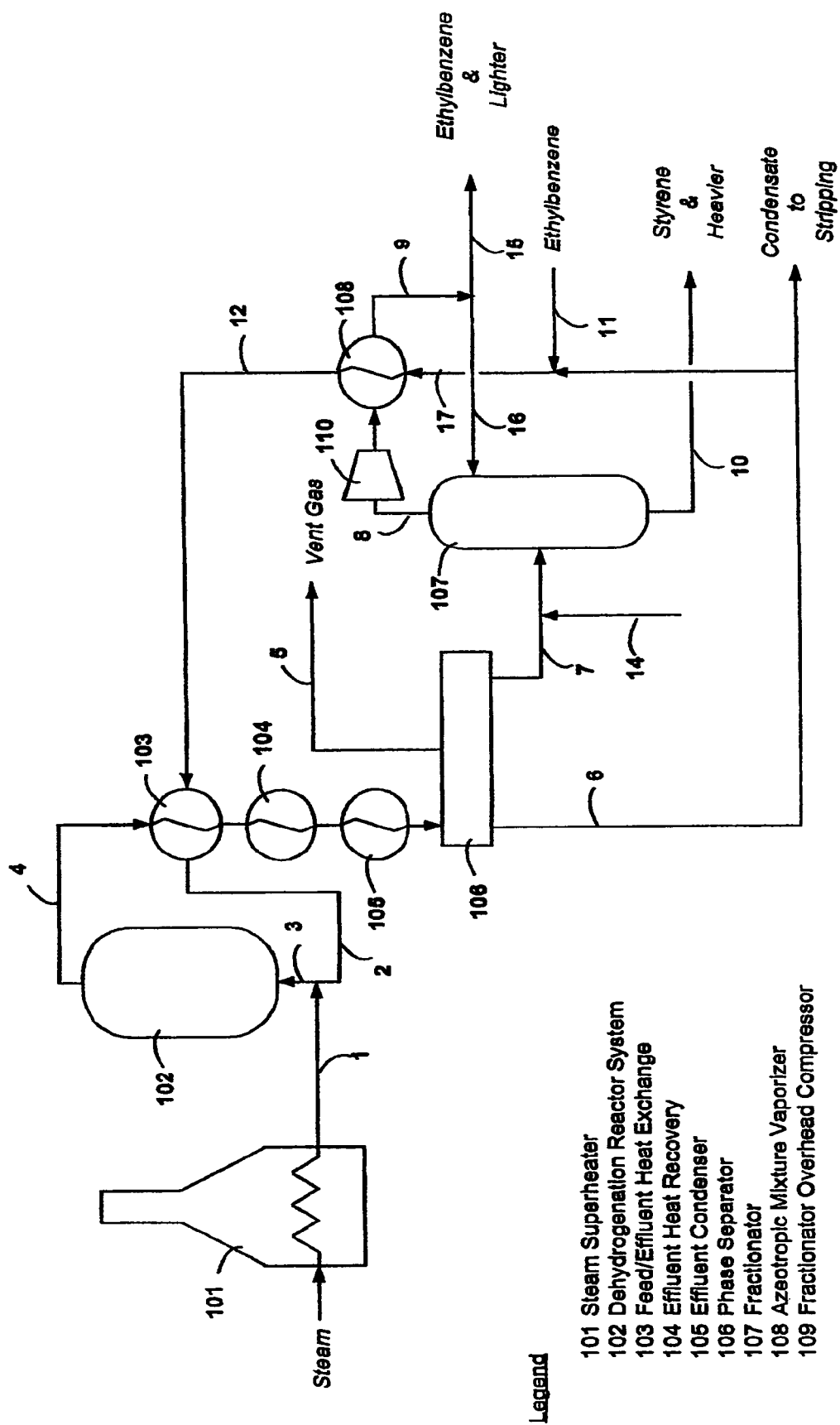
FIG. 2 is a process flow diagram of an alternative embodiment of the present invention wherein a compressor unit is located in-line between the fractionator and the condenser downstream of the fractionator.
Figure 3:
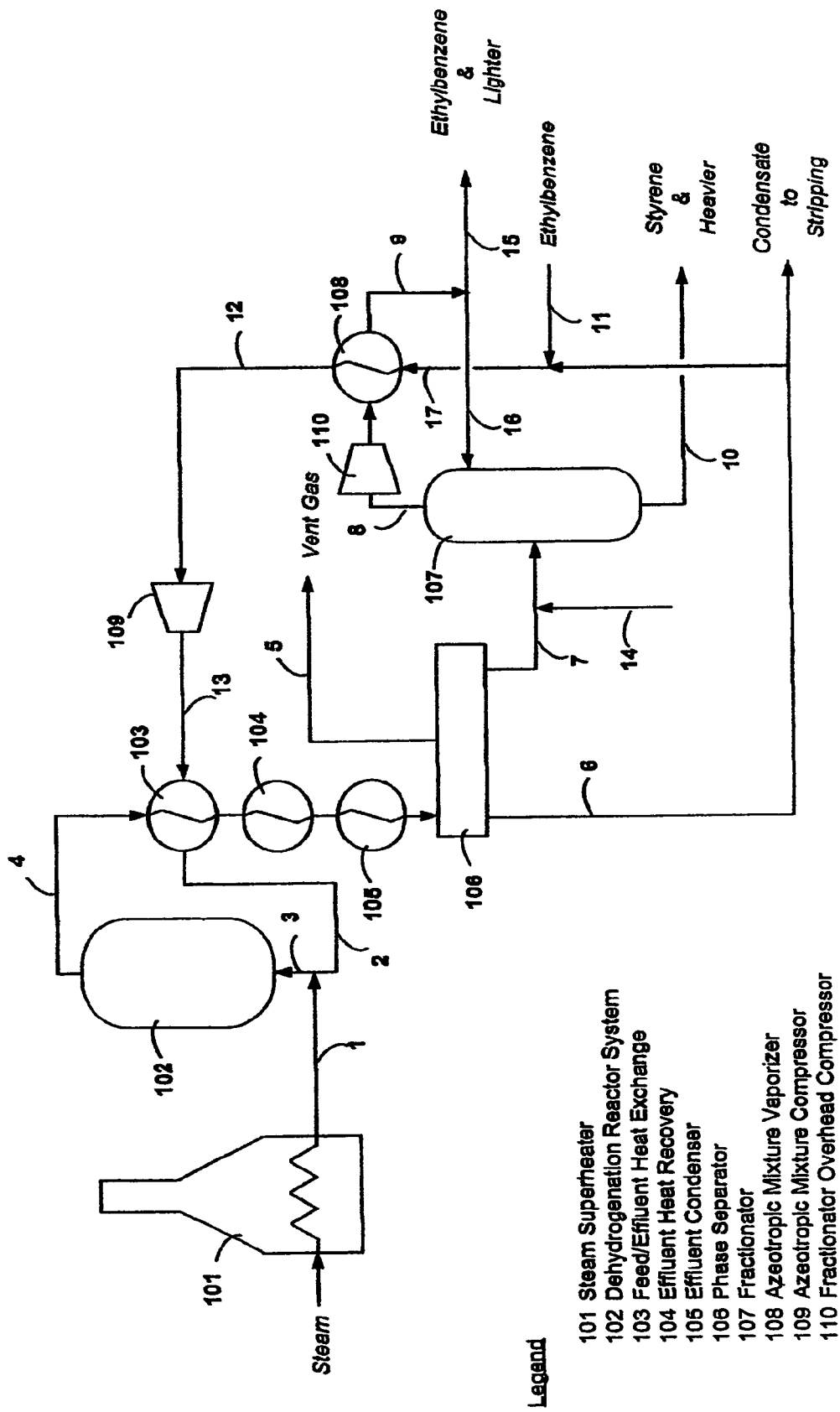
FIG. 3 is a process flow diagram of a third embodiment of the present invention which utilizes two compressor units downstream of the fractionator.
Figure 4:
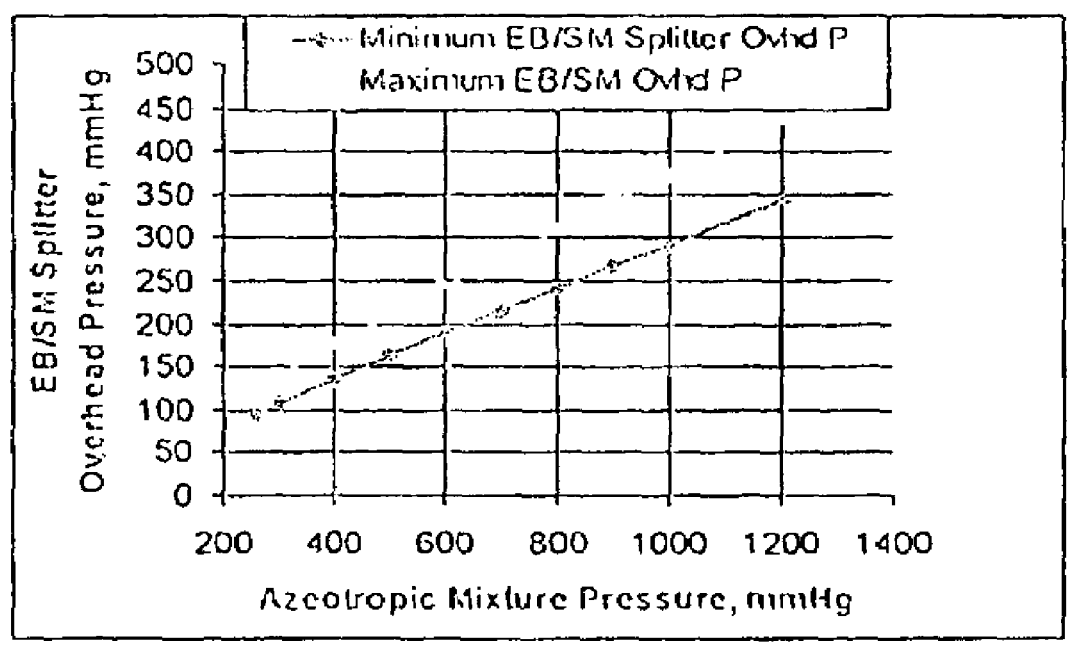
FIG. 4 is a graphical representation of a relationship between the pressure at which the azeotropic vaporization takes place and the required overhead pressure of the EB/SM splitter.

For the purposes of illustrating this invention in FIGS. 1, 2 and 3, we have chosen to present the scheme in which the first step in processing crude styrene stream 7 involves removal of ethylbenzene together with the lighter components. It will be understood, however, that the methods of the present invention are also applicable to the alternative scheme discussed above. In the scheme illustrated in FIG. 1, the crude styrene stream 7 is fed to a fractionator 107, which is preferably operated under vacuum. Operating the fractionator under vacuum is advantageous to the process in general in that it lowers the temperature of bottoms stream 10 thereby decreasing the rate of styrene polymer formation, or reducing the amount of costly polymerization inhibitor 14 which must be added to stream 7, or both. Typically, the fractionator 107 is designed to operate at an overhead pressure below 100 mmHg, which results in a bottoms stream 10 at a temperature of less than 100° C.

In prior art processes in this field, the overhead vapor stream 8 leaving the fractionator 107 is typically condensed in a condenser similar to azeotropic vaporizer 108 but utilizing either cooling water or air, which is then vented or disposed of without any heat recovery. When condensed in this manner as a step in a conventional process, the latent heat of vaporization carried by the overhead vapor stream 8 is typically rejected to the atmosphere because the temperature of this stream is too low for use in generating steam or to vaporize ethylbenzene. In accordance with the present invention, however, it has now been found that overhead vapor stream 8 can be condensed, and the heat of condensation can be used to vaporize an azeotropic mixture of ethylbenzene and water because such mixtures boil at temperatures significantly below the respective boiling points of the pure individual components.

In accordance with the methods of this invention, therefore, a fraction of about 0.30-1.0, preferably about 0.50-0.80, of overhead vapor stream 8 leaving the fractionator 107 is condensed by using it to boil a mixture of ethylbenzene and water 17 in an azeotropic condenser/vaporizer 108, which may be similar to the vaporizer described in U.S. Pat. No. 4,628,136. Other types of vaporizers, such as those described in U.S. Pat. No. 4,695,664, can also be used in carrying out the methods of this invention. U.S. Pat. Nos. 4,628,136 and 4,695,664 are incorporated herein by reference. In prior art processes, such as that taught by the U.S. Pat. No. 4,628,136 patent, the acceptable temperature differential in the condenser between the condensing fractionator overhead vapor stream and the boiling azeotropic mixture is in the range of about 2-10° C., preferably about 6° C. By contrast, the methods and apparatus of the present invention can accommodate a larger temperature differential of about 10-30° C., preferably about 15-25° C., between the condensing vapor and the boiling azeotropic mixture in vaporizer 108, leading to additional process flexibility and realizing further efficiencies.

A portion 9 of the condensed overhead, preferably a predominant portion of the condensed overhead, leaving the azeotropic vaporizer 108 is returned to the fractionator 107 as reflux stream 16, and the remainder 15 is directed to another downstream fractionator (not shown) where unreacted ethylbenzene is recovered from lighter components. This recovered ethylbenzene stream is then mixed with fresh ethylbenzene to form a combined ethylbenzene feed 11 which is returned to the system. As shown in FIGS. 1, 2 and 3, in preferred embodiments of this invention a portion of the aqueous reactor condensate 6 can be split off from the main stream and added to the combined ethylbenzene feed 11, and the resulting azeotropic ethylbenzene/water mixture 17 is then directed to the azeotropic vaporizer 108 to be boiled with heat drawn from the fractionator overhead vapor stream 8. In a further preferred embodiment of this invention, the molar ratio of water to ethylbenzene in the ethylbenzene/water mixture is between about 4-12, preferably about 6-10.

The size of the vaporizer 108 will be inversely proportional to the temperature difference between the condensing overhead vapor 9 coming from vaporizer 108 and the boiled azeotropic mixture of ethylbenzene and water 12 also coming from vaporizer 108, as determined by their respective pressures. In a prior art system, such as that described in U.S. Pat. No. 4,628,136, the pressure of the azeotropic mixture of ethylbenzene and water must be substantially above the pressure existing at the inlet to the dehydrogenation reactor section 102, typically in the range of about 400-1100 mmHg, to allow this stream to pass through the feed effluent exchanger 103 where it is preheated prior to being mixed with superheated steam 1 from stream superheater 101. As a consequence, the fractionator 107 must be operated at a pressure such that the condensing overhead temperature is at least 2° C., and preferably at least 6° C. or more, higher than the temperature of the azeotropic mixture of ethylbenzene and water going to heat exchanger 103. As a result, the temperature of bottoms stream 10 coming from fractionator 107 will necessarily be significantly higher than the optimal temperature. This higher temperature of bottoms stream 10 leads to increased formation of undesirable styrene polymer and/or requires a higher dosing rate of the costly polymerization inhibitor 14, or both.

In the practice of the present invention as illustrated in FIG. 1, however, this problem is overcome by employing an in-line compressor unit 109 between vaporizer 108 and heat exchanger 103 in order to compress the azeotropic mixture of ethylbenzene and water 12 to the pressure required for it to pass to and through the dehydrogenation reaction system 102. As a result of this innovation, the operating temperature used for fractionator 107 is decoupled from downstream pressure considerations. Fractionator 107 can thus be operated at lower, more optimal temperatures and pressures, for example at a pressure below about 200 mmHg, preferably in the range of about 70-170 mmHg, leading to lower temperatures of fractionator bottoms stream 10, which in turn minimizes undesirable polymerization of styrene in bottoms stream 10 and reduces the consumption of expensive polymerization inhibitor 14. Even with the methods and apparatus of the present invention, however, at least a small addition of a polymerization inhibitor 14 to stream 7 will generally be desirable to still further reduce the loss of styrene product. Such state-of-the-art polymerization inhibitors include those taught in U.S. Pat. Nos. 6,300,533; 6,287,483; 6,222,080; and 5,659,095, which patents are incorporated herein by reference.

In another embodiment as illustrated in FIG. 2, the fractionator overhead vapor stream 8 is compressed using compressor 110, but the azeotropic mixture of ethylbenzene and water 12 is not separately compressed. This embodiment of the present invention also facilitates decoupling the operating temperature of fractionator 107 from the pressure of the azeotropic ethylbenzene/water mixture. Because fractionator overhead vapor stream 8 coming out of compressor 110 is at a higher pressure, vaporizer 108 can correspondingly be operated at a higher pressure resulting in a higher pressure boiled azeotropic ethylbenzene/water mixture coming out of vaporizer 108.

In a yet another embodiment of this invention as illustrated in FIG. 3, both the fractionator overhead vapor stream 8 and the azeotropic mixture of ethylbenzene and water 12 are compressed, respectively, with compressor units 110 and 109. This embodiment of the present invention also facilitates decoupling the operating temperature of fractionator 107 from the pressure of the azeotropic ethylbenzene/water mixture. In comparison with the embodiments of FIGS. 1 and 2, however, the embodiment of FIG. 3 also decouples the temperature/pressure conditions in vaporizer 108 from the temperature/pressure conditions in fractionator 107, thereby creating still additional operating flexibility. In this embodiment, vaporizer 108 may be operated at any pressure (and corresponding temperature) between the temperature/pressure of fractionator 107 and the temperature/pressure required to properly feed the azeotropic ethylbenzene/water mixture to dehydrogenation reaction system 102.

All of the embodiments illustrated in FIGS. 1, 2 and 3, however, share the same advantages over the method described in U.S. Pat. No. 4,628,136, wherein no compression is used, in that they allow the fractionator 107 to be operated at a relatively low temperature and pressure, substantially the same as that of conventional processes, thereby minimizing styrene polymer byproduct, while also minimizing usage of expensive polymerization inhibitors, and while still recovering substantially all of the useful heat from the fractionator overhead vapor stream. Thus, the U.S. Pat. No. 4,628,136 patent teaches a preferred pressure of 15 psia for the azeotropic mixture of ethylbenzene and water, and a minimum (and preferred) pressure of 280 mmHg for the fractionator overhead stream, leading to a fractionator bottoms temperature of 125° C., which results in a high polymer make despite the use of a polymerization inhibitor.

By comparison, the methods and apparatus of the present invention utilize a preferred pressure of about 250-390 mmHg (5-7.8 psia) for the azeotropic mixture of ethylbenzene and water, and a preferred pressure of about 50-170 mmHg for the fractionator overhead stream (before compression), leading to a fractionator bottoms temperature of about 105° C. at the preferred overhead stream pressure, which reduces the polymer make by a factor of 4 relative to the polymer make in the process taught by the U.S. Pat. No. 6,628,136 patent. This illustrative comparison at preferred operating parameters clearly demonstrates the unexpected superiority of the present invention over the method taught by the U.S. Pat. No. 4,628,136 patent.

It will be apparent to those skilled in the art that other changes and modifications may be made in the above-described apparatus and methods for low temperature heat recovery from the overhead vapor from the EB/SM splitter in styrene manufacture without departing from the scope of the invention herein, and it is intended that all matter contained in the above description shall be interpreted in an illustrative and not a limiting sense.

What we claim is:

1. In a method of manufacturing styrene by dehydrogenation of ethylbenzene in the presence of steam at elevated temperatures in a reactor system containing a dehydrogenation catalyst, the improvement comprising the steps of:
   (a) separating the unreacted ethylbenzene from the crude styrene by fractionation in an ethylbenzene-styrene fractionator carried out at an overhead pressure below about 200 mmHg in the presence of a polymerization inhibitor;
   (b) condensing the ethylbenzene overhead vapor from the fractionator in an azeotropic vaporizer to provide heat for boiling a reactor feed consisting essentially of an azeotropic mixture of ethylbenzene and water; and,
   (c) compressing the vaporized reactor feed, the overhead vapor from the fractionator, or both to obtain an azeotropic mixture of ethylbenzene and water at a suitable pressure for feeding to the reactor system.

2. A method according to claim 1, further wherein the ethylbenzene-styrene fractionator is operated at an overhead pressure of between about 50-170 mmHg.

3. A method according to claim 1, further wherein the azeotropic mixture is boiled at a pressure of between about 250-390 mmHg.

4. A method according to claim 1, further wherein the temperature difference between the condensing overhead vapor and the boiling azeotropic mixture of ethylbenzene and water in the azeotropic vaporizer is between about 15-25° C.

5. A method according to claim 1, further wherein the fraction of overhead ethylbenzene vapor condensed in the azeotropic vaporizer is between 0.30 and 1.0.

6. A method according to claim 1, further wherein the water in the azeotropic mixture is derived from process condensate.

7. A method according to claim 1, further wherein the molar ratio of water to ethylbenzene in the reactor feed is between about 4 and 12.

8. A method according to claim 1, further wherein the pressure at the inlet to the reactor system is between about 400-1100 mmHg.

9. A method according to claim 1, further wherein said dehydrogenation catalyst consists essentially of an iron oxide based dehydrogenation catalyst.

10. A method according to claim 1, further wherein said fractionation is carried out under vacuum.

11. A method according to claim 1 wherein step (c) comprises compressing only the vaporized reactor feed.

12. A method according to claim 1 wherein step (c) comprises compressing only the overhead vapor from the fractionator.

13. A method according to claim 1 wherein step (c) comprises compressing both the vaporized reactor feed and the overhead vapor from the fractionator.

14. In a method of dehydrogenation of an alkylaromatic compound in the presence of steam at elevated temperatures in a reactor system containing a dehydrogenation catalyst, the improvement comprising the steps of:
   (a) separating unreacted alkylaromatic compound from the crude product by fractionation in a fractionator carried out at an overhead pressure below 200 mmHg in the presence of a polymerization inhibitor;
   (b) condensing the overhead vapor from the fractionator to provide heat for boiling a reactor feed consisting essentially of an azeotropic mixture of the alkylaromatic compound and water; and,
   (c) compressing the vaporized reactor feed, the overhead vapor from the fractionator, or
   both to obtain an azeotropic mixture of the alkylaromatic compound and water at a suitable pressure for feeding to the reactor system.

* * * * *